(12) United States Patent
Pagni

(10) Patent No.: US 6,497,683 B1
(45) Date of Patent: Dec. 24, 2002

(54) SYSTEM FOR HOLDING AN INDWELLING CATHETER

(76) Inventor: Larry P. Pagni, 5625 E. Horseshoe Rd., Paradise Valley, AZ (US) 85253

( * ) Notice: Subject to any disclaimer, the term of this patent is extended or adjusted under 35 U.S.C. 154(b) by 48 days.

(21) Appl. No.: 09/640,389

(22) Filed: Aug. 16, 2000

(51) Int. Cl.$^7$ ................................................ A61M 5/32
(52) U.S. Cl. ................ 604/174; 604/179; 128/DIG. 26
(58) Field of Search ................................ 604/174, 179; 128/DIG. 26

(56) References Cited

U.S. PATENT DOCUMENTS

| | | | | |
|---|---|---|---|---|
| 4,915,104 A | * | 4/1990 | Marcy | 128/207.18 |
| 4,995,384 A | * | 2/1991 | Keeling | 128/207.18 |
| 5,233,979 A | * | 8/1993 | Strickland | 128/207.14 |
| 5,549,645 A | * | 8/1996 | Frey | 604/29 |

FOREIGN PATENT DOCUMENTS

WO  WO 96/12836 A1 * 5/1996  ............ D03C/3/40

* cited by examiner

Primary Examiner—Denise L. Esquivel
Assistant Examiner—Marc Norman
(74) Attorney, Agent, or Firm—Martin L. Stoneman

(57) ABSTRACT

A system for holding an indwelling catheter above the heart of a patient wearing one. When a patient has a central line placed, the catheter is sutured into the patient's chest and the external portion of the catheter, the portion that remains outside the patient's body, must be carefully protected and kept sterile; and it must also be carefully held above the level of the patient's heart and the insertion point of the catheter so that the patient's blood does not flow back into the catheter, potentially causing life-threatening clotting or infection. A sterilizable, disposable hanger, which is connectable to the port end (the external end) of the catheter, can be suspended from a necklace or neck cord by passing the neck cord through apertures in the hanger. This system allows a patient to hang the catheter from a neck cord. Using the hanger frees patients from using tape on their skin or pins in their clothing to hold their catheter in place.

33 Claims, 3 Drawing Sheets

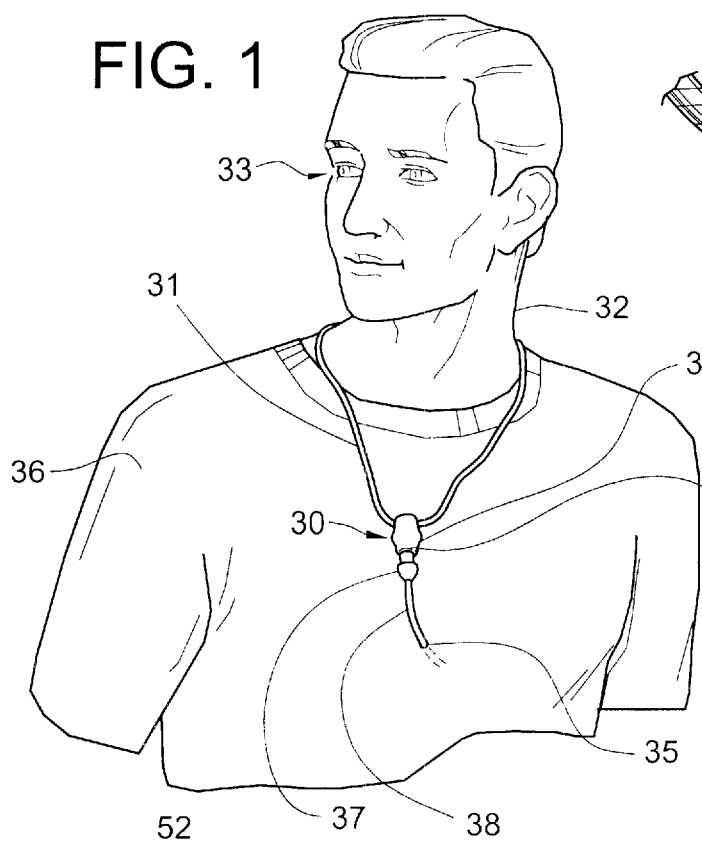
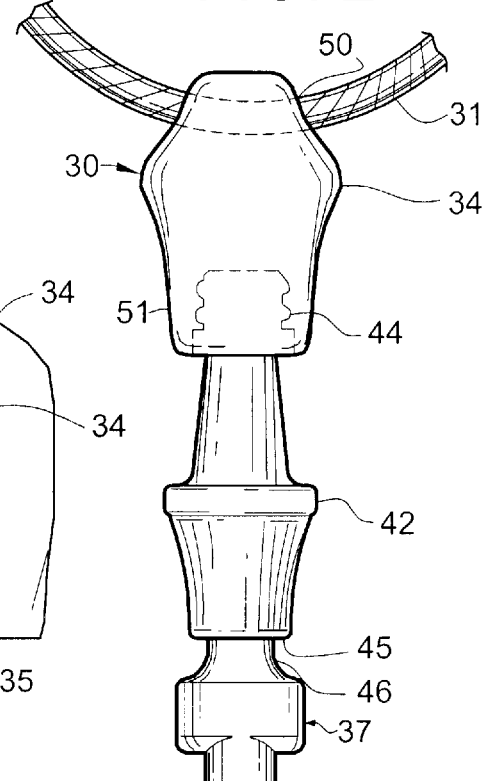
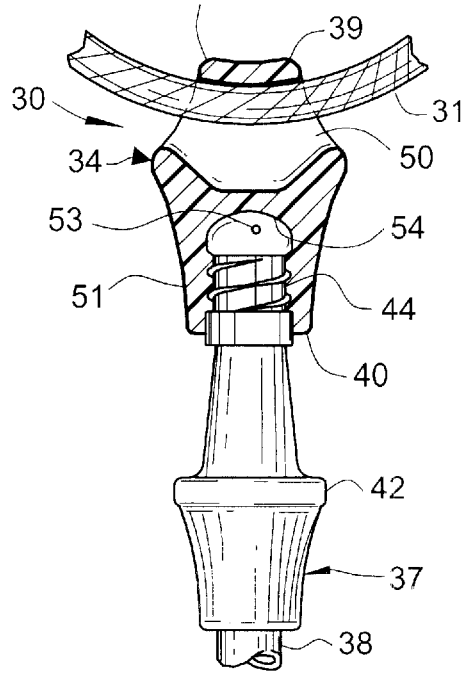
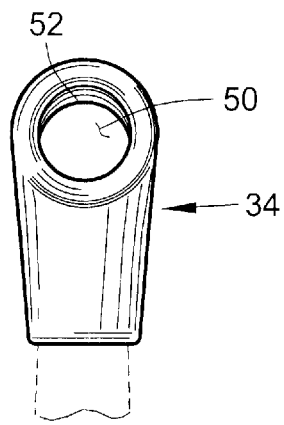
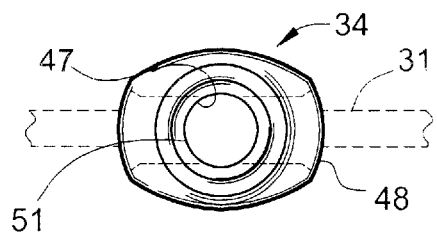

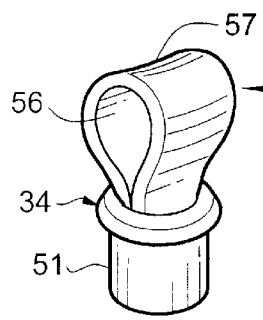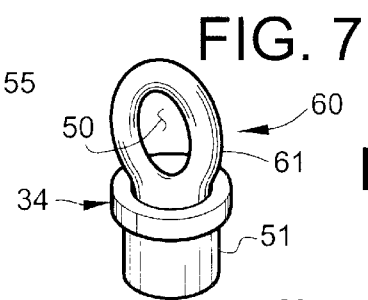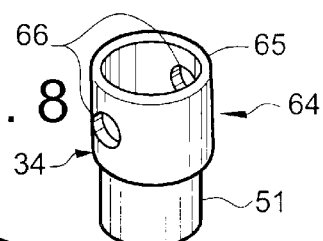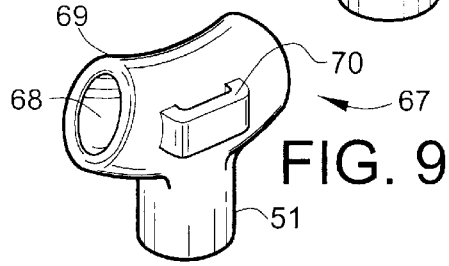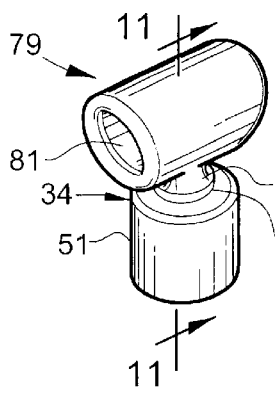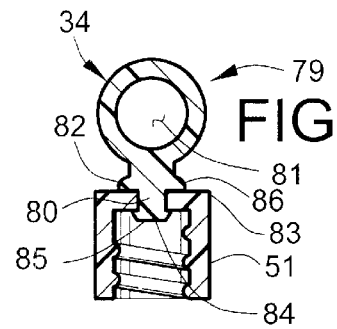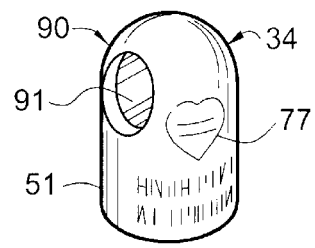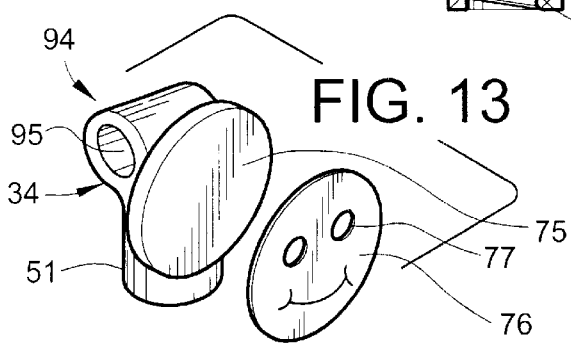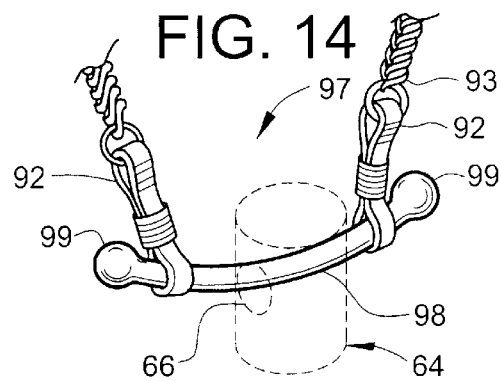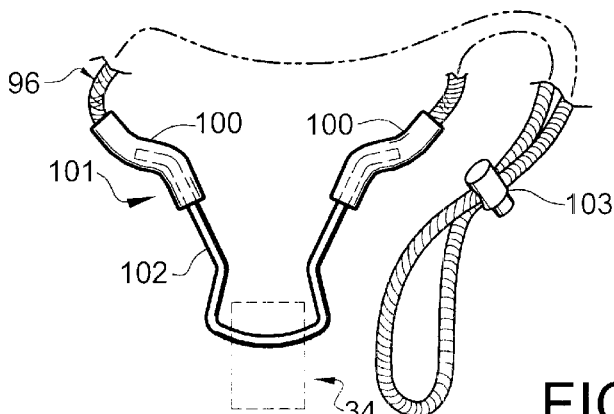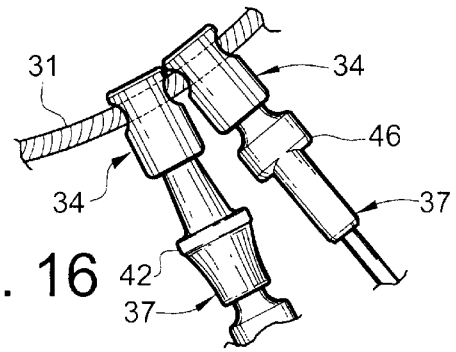

SYSTEM FOR HOLDING AN INDWELLING CATHETER

BACKGROUND

People with medical conditions which require indwelling catheters (usually venous), chronic or acute, for the delivery of drugs find that these catheters are uncomfortable and difficult to maintain. Indwelling catheters allow medical professionals to deliver intravenous medications continuously or repeatedly without repeatedly puncturing a vein. For example, cancer patients who require continuous infusions of chemotherapeutic agents receive their medications through indwelling catheters. For the medical professional, these indwelling catheters are a necessary convenience. For the patient, these catheters are uncomfortable, difficult to keep clean and sterile, and easy to pull out. They also represent a significant risk of life-threatening systemic infection.

Chronic indwelling catheters are surgically inserted into a vein through the patient's chest wall and are sutured to the patient's skin to prevent the insertion end from slipping out. These catheters can be in place for months or even years at a time. Typically, the external port end of the catheter is looped and secured to the skin with tape or is pinned to the patient's shirt, undergarment or bra. Movement and exercise are made difficult and uncomfortable if the clothing that the catheter is pinned to moves in relation to the insertion point of the catheter. Sometimes, the catheter is accidentally pulled out because the patient forgets to detach it from their clothing when undressing. Such problems occur even in acute such catheter use for a brief time.

Patients find that sleeping is especially uncomfortable with one of these catheters in place. These catheters are often pulled out during sleep. For example, if the catheter is pinned to a garment and the garment is not carefully adjusted when the patient rolls over during sleep, the catheter can easily be pulled out. Patients have difficulty sleeping because of worry over losing their catheters, soiling the bed sheets with blood, and risking infection. Patients who secure their catheters with tape may develop rashes or allergic reactions to the adhesive from the tape. Hirsute patients may be forced to either shave their chests or experience the pain of taped hair. Tape with less adhesive may lose its strength in hot weather when the patient perspires. Strongly adhesive surgical tape is uncomfortable to remove for daily treatments, especially after months of using tape in the same location.

The insertion point of these catheters is often the site of infection. Infection at the site of an indwelling catheter can follow the catheter directly into the bloodstream, creating life-threatening systemic infection. To prevent this serious infection, patients are charged with the responsibility of keeping the insertion point clean and sterile. The catheter itself must also be kept clean and the patient is often required to flush the catheter with saline. To further complicate the maintenance of these catheters, if the port end of the catheter falls below the insertion site or the level of the patient's heart, venous backflow or siphon effect can occur. This backflow seriously increases the risk of infection and clotting.

Often, whether these catheters are taped to the patient's chest or pinned to clothing, they are visible through shirts and clothing worn by the patient. The catheters are especially visible when taped to the most prominent area of the patient's pectoral muscle or pinned to the undergarment, shirt or bra. Patients find these catheters to be unsightly and embarrassing, a visible reminder of their illness.

OBJECTS

It is an object and feature of this invention, preferred forms of which are described in detail hereinafter, to overcome these disadvantages and drawbacks and to provide significant improvements in the care and maintenance of indwelling catheters not previously available.

It is an object and feature of this holding system to allow the external port end of the catheter to be suspended from the patient's neck. This holding system allows patients to wear their catheters like jewelry. Using this holding system, patients can wear their catheters discretely so that they hang midline on the chest, like jewelry, instead of being pinned prominently on the patient's undergarment, shirt or bra or taped prominently on the patient's pectoral muscle.

It is an object and feature of this invention to keep the port end from dropping below the level of the insertion end and the level of the patient's heart, and therefore reduce the risk of infection and clot-causing backflow or siphon effect. It is an object and feature of this invention to maintain the port end in a position carefully maintained by the length of the suspending element. It is also an object and feature of this invention to provide a sterile and sterilizable contact point between the catheter and holding system to help the patient fight infection.

This holding system, in a preferred form, also provides a holding system which does not require the use of uncomfortable, painful or rash-causing tape. It is an object and feature of this invention, to provide a holding system which allows patients to sleep without worrying so much that changing sleeping positions might rip the catheters from their chests. This holding system, in a preferred form, provides a holding system which allows patients to disrobe without worrying that changing clothes might rip the catheters from their chests.

It is an object and feature of this invention to provide a holding system which allows patients a greater range of motion. It is also an object and feature of this invention to reduce the patient's worry that exercise or movement will cause their catheter to be pulled out. It is a further object and feature of this invention to provide that advertising or decorative materials can be attached to the holding system. For example, children can affix stickers or other decorative materials to a preferred form of this holding system.

SUMMARY

According to a preferred embodiment of the present invention, this invention provides a holder system for comfortably and flexibly holding a port end of an indwelling catheter above a heart of a patient comprising: catheter cap means for releasably holding the port end of the indwelling catheter; hanging means for being suspended by a neck cord; wherein such hanging means comprises such catheter cap means and connection means for connecting with the neck cord. And it provides such system wherein such connector means comprises extension means, extending from a main body of such hanging means, for assisting connection with an eyeglass-holder neck cord. It also provides such a system wherein said connection means comprises an aperture and such system further comprises an adapter means for attaching with the neck cord and passing through such aperture means. Further it provides such system wherein such adapter means comprises a rigid bar portion suitable to pass through such aperture.

It further provides such system wherein such hanging means further comprises a divider means, between such aperture means and such catheter cap means, for assisting maintaining the sterility of the port end of the indwelling catheter. Further, it provides such system comprising suspending means for suspending such hanging means above the heart of the patient. It also provides such system wherein such suspending means comprises the neck cord. It also provides such system comprising a second such hanging means, wherein each such hanging means is suspended by the same such suspending means.

According to a preferred embodiment of the present invention, this invention provides a holder system for comfortably and flexibly holding a port end of an indwelling catheter above a heart of a patient comprising a catheter cap structured and arranged to releasably hold the port end of the indwelling catheter; a hanger structured and arranged to be suspended by a neck cord; wherein such hanger comprises: such catheter cap; and, at least one aperture structured and arranged to hold the neck cord. It further provides such system comprising an adapter structured and arranged to pass through such aperture. Also, it provides such system wherein such adapter is structured and arranged to attach to the neck cord. Even further, it provides such system wherein such hanger further comprises a divider between such aperture and such catheter cap structured and arranged to assist maintaining sterility of the port end of the indwelling catheter. It further comprises such system wherein such divider comprises a dome. Even further, it provides such system wherein such divider comprises a small hole structured and arranged to assist in preventing back air pressure on the catheter.

It also provides such system wherein such hanger further comprises indicia. Moreover, it provides such system wherein such hanger further comprises a hook. It also provides such system wherein such indicia is removably attached to such hanger by hanging such indicia from such hook. Further, it provides such system wherein such aperture comprises a sliding connection with the neck cord. Even further, it provides such system wherein such hanger comprises a anti-kinker to assist in preventing kinking in the indwelling catheter. Still further, it provides such system wherein such anti-kinker comprises a swivel connection between such catheter cap and such aperture. It also provides such system wherein such anti-kinker is structured and arranged to limit movement of such hanger with respect to the neck cord.

It also provides such system further comprising a suspender structured and arranged to suspend such hanger above the heart of the patient. Additionally, it provides such system wherein such suspender comprises the neck cord. In addition, it provides such system further comprising at least one second such hanger, wherein each such hanger is suspended by the same such suspender.

It also provides such system wherein such suspender further comprises an eye-glass holder adapter constructed and arranged to fit through such at least one aperture. Further, it provides such system wherein such eye-glass holder adapter comprises a rigid bar portion. Still further, it provides such system wherein such aperture comprises an internally convex curve structured and arranged to assist such aperture to move slidingly along the neck cord. And it provides such system wherein such aperture comprises a tunnel shape. Moreover, it provides such system wherein such hanger comprises at least two apertures.

Still further, it provides such system wherein such aperture comprises a ring. And it provides such system wherein such hanger comprises essentially a disposable plastic material. Further, it provides such system wherein such hanger comprises jewelry-grade metal. It also provides such system wherein: such aperture comprises a sliding connection with the neck cord; such hanger comprises an anti-kinker to assist in preventing kinking in the indwelling catheter; and such hanger comprises essentially a disposable plastic material. And it provides such system further comprising a suspender structured and arranged to suspend such hanger above the heart of the patient. And it provides such system wherein such suspender comprises an eye-glass holder adapter constructed and arranged to fit through such at least one aperture.

Even moreover, in accordance with a preferred embodiment thereof, this invention provides a holder system to comfortably and flexibly hold a port end of an indwelling catheter above a heart of a patient comprising: an indwelling catheter having a port end; a catheter cap structured and arranged to releasably hold such port end of such indwelling catheter; a hanger structured and arranged to be suspended by a neck cord; and a suspender structured and arranged to suspend such hanger above the heart of the patient, such suspender comprising the neck cord; wherein such hanger comprises such catheter cap, and at least one aperture structured and arranged to hold such suspender.

BRIEF DESCRIPTION OF THE DRAWINGS

FIG. 1 is a front view of a preferred embodiment of the holding system as it might appear when worn by a patient.

FIG. 2 is an enlarged front view of a preferred embodiment of the holding system of FIG. 1.

FIG. 3 is a partial cross-sectional front view of a preferred embodiment of the holding system of the present invention.

FIG. 4 is a side view of the preferred embodiment of FIG. 1 illustrating the tunnel through which the suspender threads.

FIG. 5 is a bottom view looking up through the preferred embodiment of FIG. 1.

FIG. 6 is a perspective view illustrating another preferred embodiment of the holding system.

FIG. 7 is another perspective view illustrating another preferred embodiment of the holding system.

FIG. 8 is another perspective view illustrating another preferred embodiment of the holding system.

FIG. 9 is another perspective view illustrating another preferred embodiment of the holding system.

FIG. 10 is another perspective view illustrating another preferred embodiment of the holding system illustrating a swivel.

FIG. 11 is a cross-sectional side view of the holding system of FIG. 10.

FIG. 12 illustrates another preferred embodiment of the holding system, illustrating advertising or other decoration.

FIG. 13 is another perspective view illustrating another preferred embodiment of the holding system, illustrating how advertising or decorative stickers may be applied to the holding system.

FIG. 14 is another perspective view illustrating the suspender system in one of its preferred embodiments.

FIG. 15 is a front view illustrating another preferred embodiment of the suspender system.

FIG. 16 is a front view illustrating a preferred embodiment of the present invention, accommodating more than one catheter port.

DETAILED DESCRIPTION OF THE PREFERRED EMBODIMENTS AND BEST MODES OF PRACTICE

Figure 17:
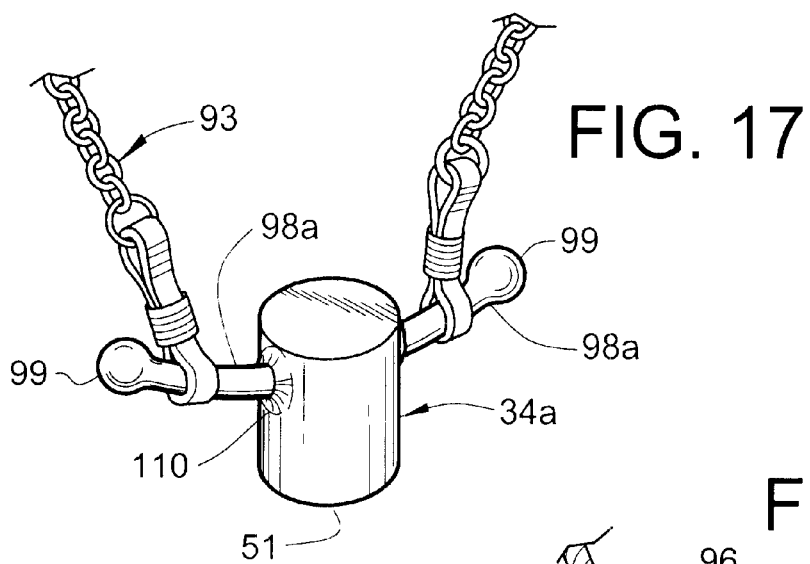
FIG. 17 is a perspective view illustrating an alternate embodiment of the holder system of the present invention, utilizing a similar suspender system to that of FIG. 14 but showing an alternate embodiment of the hanger.

As FIG. 1. illustrates, a preferred embodiment of the holding system 30 (embodying herein a holder system for comfortably and flexibly holding a port end of an indwelling catheter above a heart of a patient) of the present invention may be worn by a patient 33. The holding system 30 preferably includes suspender 31 and hanger 34 (embodying herein hanging means for being suspended by a neck cord). Hanger 34 preferably includes aperture 50 (as illustrated in FIG. 4) through which suspender 31 may be threaded, and catheter cap 51 (embodying herein catheter cap means for releasably holding the port end of the indwelling catheter, and embodying herein hanging means comprising such catheter cap means and connector means for connecting with such neck cord, and also embodying herein a catheter cap structured and arranged to releasably hold the port end of the indwelling catheter, and even further embodying herein such hanger comprising such catheter cap and at least one aperture structured and arranged to hold the neck cord). Suspender 31 is preferably of the type which goes around a neck 32 of a patient 33; and suspender 31 is preferably a neck cord, i.e., a flexible material of small and relatively constant cross-section, although it may in certain cases be suitable that necklaces, jeweled or not, even not of constant cross-section, will be appropriate (embodying herein the neck cord). Hanger 34 (embodying herein a hanger structured and arranged to be suspended by a neck cord) is preferably attached slidingly to suspender 31. As FIG. 1 also illustrates, preferably attached to hanger 34 is port end 37 of catheter 38. Port end 37 normally includes the actual catheter port plus universal needleless connector 42 whose male end 44 connects to catheter cap 51 of hanger 34 (catheter 38 embodying herein such catheter comprising a port end).

As illustrated in FIG. 1, suspender 31 is preferably of an appropriate length to maintain port end 37 of catheter 38 above the level of the patient's heart and above the level of the insertion point (of the indwelling catheter) through the patient's chest (suspender 31 embodying herein a suspender structured and arranged to suspend such hanger above the heart of the patient). Because the preferred length of suspender 31 is different for each patient, depending on the patient's size, the length of suspender 31 is preferably adjustable. When suspender 31 is a preferred length, the risk of retrograde venous flow, backflow or siphon effect, is reduced. Retrograde venous flow, backflow or siphon effect may cause infection or clotting. Preferably, suspender 31 also maintains the position of the port end 37 of catheter 38 midline on the chest below the sternoclavicular junction, anterior to the manubrium, and inferior to the jugular notch.

In FIG. 1, holding system 30 is shown hanging outside a shirt 36 for the purposes of illustration. FIG. 1 shows catheter 38 disappearing inside a shirt through hole 35. Alternately, holding system 30 is worn so that it hangs underneath shirt 37, hidden from view.

FIG. 2 illustrates in enlarged front view the preferred embodiment of FIG. 1. As FIG. 2 illustrates, suspender 31 (embodying herein suspending means for suspending such hanging means above the heart of the patient) preferably slidingly holds hanger 34, which is connected to port end 37 of catheter 38, shown with a clamp 43 on it. Universal needleless connector 42 is preferably a disposable sterilizable connector with a male end 44 and a female end 45 such as a Clave (R). [Clave (R) is a registered Trademark of ICU Medical, San Clemente, Calif., is readily available from medical supply sources and is well known in the art.]

Catheter 38 is preferably an indwelling catheter, typically a chronic tunneled central venous catheter with a male-ended adaptor 46 such as a Hickman (R), Broviac (R), Leonard(R) or Groshong (R). [Hickman (R), Broviac (R), Leonard(R) and Groshong(R) are Trademarks of C.R. Bard, Inc., Murray Hill, N.J., 07974, are readily available from medical supply sources and are well known in the art.)] Catheter 38, even without a universal needleless connector 42, typically has a male-ended port end 44a (see FIG. 2) of adaptor 46 which will properly connect directly to the interior threads of the catheter cap 51 (see FIG. 2) of the holder system of the present invention.

FIG. 3 is a partial cross-sectional view of the preferred embodiment as shown in FIG. 2. FIG. 3 illustrates hanger 34 in cross-section. Hanger 34 has a top end 39 and a bottom end 40. Top end 39 of hanger 34 preferably includes an aperture 50 through which suspender 31 is shown passing (for connecting hanger 34 with suspender 31). Aperture 50 is preferably sealed-off (as illustrated) from catheter cap 51 by a sealed divider 54 (embodying herein that such hanging means further comprises a divider means, between such aperture means and such catheter cap means, for assisting maintaining the sterility of the port end of the indwelling catheter; and also embodying herein that such hanger further comprises a divider between such aperture and such catheter cap structured and arranged to assist maintaining sterility of the port end of the indwelling catheter), preferably dome-shaped, (embodying herein that such divider comprises a dome) so that catheter cap 51 can maintain a sterile environment, separated from the non-sterile suspender 31. As FIG. 3 also illustrates, aperture 50 preferably includes a curve 52 to facilitate sliding movement of hanger 34 along suspender 31. The bottom end 40 of hanger 34 also preferably includes catheter cap 51. Catheter cap 51 is preferably interiorly threaded (see FIG. 2) to receive the port end 37 of a catheter (with or without a universal needleless connector).

FIG. 3 also illustrates that catheter cap 51 may preferably include a very small hole 53 to allow air to escape when threaded male end 44 of universal needleless connector 42 is threaded securely into female-end threaded catheter cap 51. This very small hole 53 (embodying herein that such divider comprises a small hole structured and arranged to assist in preventing back air pressure on the catheter) may reduce the risk of infection and clotting by allowing air to escape and reducing air pressure against universal needleless connector 42 and catheter 38 when the two ends are screwed together.

FIG. 4 is a side view of holding system 34 (of the embodiment of FIG. 1) illustrating aperture 50 through which the suspender threads. Aperture 50 is preferably large enough to accommodate suspender 31 without constricting suspender 31 or restricting the sliding movement of hanger 34 (embodying herein that such aperture comprises a sliding connection with the neck cord) in any way. FIG. 4 also illustrates preferred curve 52 in side-view.

FIG. 5 is a bottom view of hanger 34 illustrating a preferred embodiment of female-end threaded catheter cap 51. The internal features 47 of this region are preferably constant through all of the different embodiments of FIGS. 1–16 because, in each of these embodiments, it must accommodate a standard male end 44 of universal needleless connector 42 (or the similar port end 44a of the indwelling catheter adaptor). However, the external shape 48 of catheter cap 51 may be changed for decorative or practical purposes. For example, it may be preferable for the external shape 48 of catheter cap 51 to be more flattened or oval than round so that hanger 34 will lay flatter with less rotation against a patient's chest.

FIG. 6 is a perspective view illustrating another preferred embodiment 55 of hanger 34 of the present invention. Embodiment 55, illustrated in FIG. 6, preferably includes a female-end threaded catheter cap 51 which can receive a male-end threaded universal needleless connector 42 described above (or port end of the catheter without the connector 42, as stated previously), and aperture 56. Aperture 56 preferably has a different shape compared with that described in FIGS. 3 and 4, but which serves the same purpose. Aperture 56 is preferably large enough to accommodate suspender 31 (as illustrated in FIG. 3) without constricting suspender 31 or restricting the sliding movement of embodiment 55 along suspender 31 in any way. FIG. 6 also illustrates a slight curve 57 (externally concave and internally convex) in aperture 56 to facilitate sliding movement along suspender 31. In another preferred embodiment, aperture 56 may be smaller for the purpose of limiting sliding movement of hanger 34 along suspender 31. It might be preferable to restrict sliding movement to decrease the risk of the catheter kinking or otherwise becoming entangled.

FIG. 7 is another perspective view illustrating another preferred embodiment 60 of hanger 34. Embodiment 60 preferably includes a female-end threaded catheter cap 51 which can receive male-end threaded universal needleless connector 42 described above, and ring 61 (another form of aperture 50 and the other aperture forms herein illustrated). Suspender 31 (as illustrated in FIG. 3) can be threaded through ring 61. Ring 61 is also preferably shaped to allow embodiment 60 of hanger 34 to move slidingly along suspender 31 without constricting suspender 31 or restricting the sliding movement of embodiment 60 along suspender 31 in any way.

FIG. 8 is another perspective view illustrating another preferred embodiment 64 of hanger 34. Embodiment 64 preferably includes a female-end threaded catheter cap 51 attached to a two-aperture suspender holder 65 (embodying herein at least two apertures). The two-aperture holder 65 preferably includes two apertures 66 through which suspender 31 can be threaded. Suspender holder 65 is also preferably shaped to allow embodiment 64 of hanger 34 of the present invention to move slidingly along suspender 31 without constricting suspender 31 or restricting the sliding movement of embodiment 64 along suspender 31 in any way.

FIG. 9 is another perspective view illustrating another preferred embodiment 67 of hanger 34 of the present invention. As FIG. 9 illustrates, tunnel-type aperture 68 preferably includes a curve 69 (embodying herein an internally convex curve structured and arranged to assist such aperture to move slidingly along the neck cord) for assisting embodiment 67 to move slidingly along suspender 31 (as also shown in FIG. 3). As FIG. 9 also illustrates, a hook 70 is preferably attached to the outside of embodiment 67. Hook 70 preferably allows for the attachment of a surface 75 (as shown in FIG. 13) for attaching advertising material, decorative stickers 76 or other indicia 77 on visible portion of preferred embodiment 67 of the present invention. The back side of surface 75 preferably contains a clip (not shown) which can slide through hook 70 to removably attach in a well-known manner a surface 75 to preferred embodiment 67.

FIGS. 10 and 11 illustrate another preferred embodiment 79 of hanger 34. In FIGS. 10 and 11, the aperture element 81 is tunnel-shaped (embodying herein a tunnel shape). FIGS. 10 and 11 illustrate a preferred rotatable attachment 80 (or swivel) between catheter cap 51 and aperture 81. FIG. 11 is a cut-away side view of embodiment 79 through the section 11—11 of FIG. 10. As shown in FIG. 11, aperture element 81 is preferably manufactured as a separate piece from catheter cap 51 of hanger 34. Bottom end 84 of aperture element 81 is preferably conical in shape, with bottom end 84 being smaller in cross-sectional diameter than top end 86, with groove 82 being preferably situated between bottom end 84 and top end 86. Annular flange 83 of catheter cap 51 is preferably flexible enough to flex outward so that the two pieces, aperture element 81 and catheter cap 51 can preferably be attached together by pushing bottom end 84 of aperture element 81, with its conical shape, down into catheter cap 51, so that annular flange 83 flexes outward just enough to accommodate the slight increase in diameter of the conical bottom end 84 of the aperture element 81 until annular flange 83 is seated into groove 82 of catheter cap 51. Annular flange 83 at the top of catheter cap 51 preferably fits rotatably into groove 82. When attached together, with annular flange 83 seated into groove 82 of catheter cap 51, aperture element 81 can preferably rotate bidirectionally 360 degrees in relation to catheter cap 51 (embodying herein an anti-kinker to assist in preventing kinking in the indwelling catheter; and also embodying herein that such anti-kinker comprises a swivel connection between such catheter cap and such aperture).

FIG. 12 illustrates another preferred embodiment 90 of hanger 34, showing advertising or other decorative indicia 77 directly applied to embodiment 90. Embodiment 90 preferably includes a female-end threaded catheter cap 51 which can receive, e.g., the male-end threaded 44 universal needleless connector 42 described above, and aperture 91. Embodiment 90 also preferably includes aperture 91 (with a different shape compared with those described in previous figures, but which serves the same purpose). Aperture 91 is also preferably large enough in diameter to accommodate suspender 31 (as illustrated in FIG. 3) without constricting suspender 31 or restricting the sliding movement of embodiment 91 along suspender 31 in any way.

FIG. 13 is another perspective view illustrating another preferred embodiment 94 of hanger 34. Embodiment 94 preferably includes a female-end threaded catheter cap 51 which can receive the male-end threaded 44 universal needleless connector 42 (See FIG. 3), and aperture 95. Embodiment 94 preferably includes aperture 95 with a different shape compared with that described in FIGS. 2–12, but which serves the same purpose. Aperture 95 is preferably large enough to accommodate suspender 31 (as illustrated in FIG. 3) without constricting suspender 31 or restricting the sliding movement of embodiment 94 along suspender 31 in any way.

FIG. 13, mentioned previously, also illustrates that advertising or decorative stickers 76 containing indicia 77 (embodying herein indicia), such as cartoon characters, may be applied to surface 75. Surface 75 may be preferably clipped to hook 70 (as illustrated in FIG. 9) embodying herein that such indicia is removably attached to such hanger by hanging such indicia from such hook. Surface 75 is preferably attached to hanger 34, as illustrated in embodiment 94, by glueing, welding, or another suitable type of adhesive process. Surface 75 may, in another embodiment, be manufactured to be integral with hanger 34. For example, surface 75 may be manufactured in the same mold as the rest of embodiment 94 when a plastic embodiment is made. In other preferred embodiments, decorative features such as bola ties or charms can be clipped to hook 70.

Advertising material may be in the form of embossed plastic or metallic indicia. Decorative indicia are particularly appealing for pediatric patients who may find their catheters to be embarrassing and unwieldy. Physicians may choose to give stickers to their pediatric patients when these patients visit for treatment. The ability to decorate their catheters and change the decorations on their catheters may increase compliance among pediatric patients.

FIG. 14 is a perspective view illustrating a preferred embodiment of suspender system 97. In this preferred embodiment 97, suspender 93 is an eyeglass holder with plastic loop adapters 92; however suspender 93 may be adapted to support/suspend a hanger of the present invention by means of a rigid adapter 98, a preferably cotton-swab-shaped stiff rod (embodying herein that such adapter means comprises a rigid bar portion suitable to pass through such aperture means). Adapter 98 allows a patient to use commonly available eyeglass-holders to suspend their catheters 38 around their necks 32 (See FIG. 1). FIG. 14 illustrates adapter 98 as it would pass through a two-hole holder 64, shown in dotted lines (and as illustrated in FIG. 8). Adapter 98 (embodying herein an adapter structured and arranged to pass through such aperture) would preferably slide through any of the aperture embodiments illustrated in FIGS. 1–13. When suspender 31 has an plastic loop adapter 92 on it, enlarged ends 99 will keep the eyeglass-holder adapter 92 from sliding off the ends 99 of adapter 98.

FIG. 15 is a front view illustrating another preferred embodiment 101 of suspender system 96. Suspender system 96 includes eyeglass holders with plastic tube adapters 105. Suspender system 96 attaches to a modified-U-shaped rigid adapter 102 (embodying herein such eye-glass holder adapter comprising a rigid bar portion) which allows a patient to use the plastic tube adapters 100 type of commonly available eyeglass holders to suspend their catheters 38 around their necks 32 (embodying herein an eye-glass holder adapter constructed and arranged to fit through such at least one aperture). In this preferred embodiment 101, U-shaped-rod adapter 102 suspends hanger 34 in a predictable position. U-shaped rod adapter 102, by limiting the sliding movement of hanger 34 along suspender system 96, may limit kinking in the catheter (embodying herein that such anti-kinker is structured and arranged to limit movement of such hanger with respect to the neck cord). Hanger 34 will be restricted in its ability to slide along adapter 102 but will still be able to rotate around U-shaped adapter 102. FIG. 15 also illustrates that a suspender 31 may preferably have an adjustable element 103 for the purpose of adjusting the length of suspender 31 in well-known ways.

FIG. 16 is a front view illustrating a preferred embodiment of the present invention suspending on a suspender 31 more than one hanger 34 (embodying herein a second such hanging means, wherein each such hanging means is suspended by the same such suspending means and also embodying herein a second such hanger, wherein each such hanger is suspended by the same such suspender), preferably up to three hangers 34 since multiple-port indwelling catheters may at times have two or three ports. FIG. 16 also illustrates that the catheter cap of the present invention may be connected with either a male-end threaded universal needleless connectors 42 (shown connected to one hanger 34) or directly with the adaptor end 44a of the adaptor 46 of the indwelling catheter (shown connected to the other hanger 34).

In a preferred embodiment, suspender 31 can be made of washable and/or disposable material such as string, nylon or cotton cording, decorative materials such as gold, silver or other metal chain, or leather. These materials thread through any of the preferred aperture features illustrated in FIGS. 1–16 and are adjustable by altering the length of the materials. Suspender 31 can also preferably be eyewear retainers or eyeglass-holders such as those available from Croakies (™), Fields Accessories (™), Shockers (™), King Link (™) eyeglass holders or Corinne McCormack, Inc. (TM), used in association with an adapter such as U-shaped rod 102 (See FIG. 15) or rod 98 (see FIG. 14) or any other similar/suitable adapter of the type illustrated of the present invention. Eyeglass holders are commonly available and are normally adjustable (see FIG. 15).

FIG. 17 is a perspective view of another preferred embodiment of the holder system of the present invention, utilizing a similar suspender system to that of FIG. 14 but showing an alternate embodiment of the hanger. Hanger 34a also includes a catheter cap 51 at its bottom end but does not include any apertures (as for other hangers 34). Instead, hanger 34a utilizes adapter portions 98a, similar in purpose to adapter 98 of FIG. 14 but being a unitary part of hanger 34a rather than requiring apertures in hanger 34 for support. Preferably, there will be included a suitable radius 110 to provide additional strength to the juncture between adapter portions 98a and the main body portion of hanger 34a. Eyeglass holder 93 is preferably connected with adapter portions 98a similarly as for the suspender system of FIG. 14.

Figure 18:
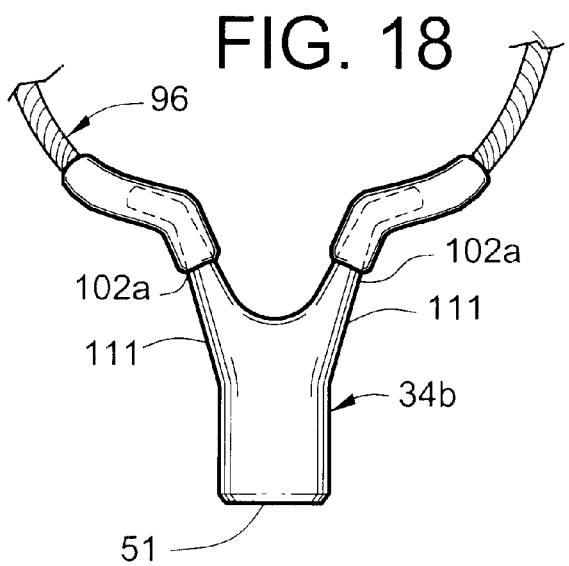
FIG. 18 is a perspective view illustrating another alternate embodiment of the holder system of the present invention, utilizing a similar suspender system to that of FIG. 15 but employing yet another alternate embodiment of the hanger.

FIG. 18 is a perspective view illustrating another alternate embodiment of the holder system of the present invention, utilizing a similar suspender system to that of FIG. 15 but employing yet another alternate embodiment of the hanger. Hanger 34b also includes a catheter cap 51 at its bottom end but does not include any apertures (as for other hangers 34). Instead, hanger 34b utilizes adapter portions 102a, similar in purpose to adapter 102 of FIG. 15 but being a unitary part of hanger 34b rather than requiring apertures in hanger 34 for support. Preferably, there will be included a suitable strengthening portions 111 to provide additional strength to the junctures between adapter portions 102a and the main body portion of hanger 34b. Eyeglass holder 96 is preferably connected with adapter portions 102a similarly as for the suspender system of FIG. 15.

Figure 19:
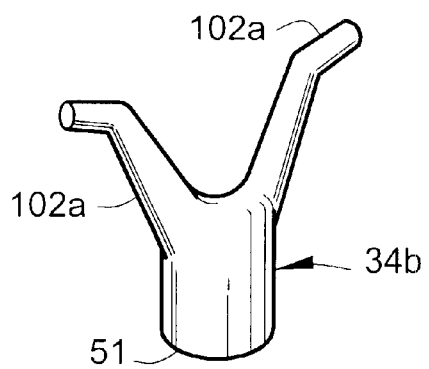
FIG. 19 is a perspective view of the hanger embodiment of FIG. 18.

FIG. 19 is a perspective view of the hanger embodiment 34b of FIG. 18, illustrated without eyeglass holder 96 attached.

Any of the hanger embodiments illustrated in FIGS. 1–19, including the hanger 34 and suspender elements 98 and 101 may preferably be made of moldable or injectable, preferably disposable, plastic (embodying herein essentially a disposable plastic material); and for suitable purposes, may be made of metal, including gold, silver, brass or other decorative metals (embodying herein jewelry-grade metal). In a preferred embodiment, hanger 34 is sterilizable, lightweight, inexpensive, easy to use, and can be sold in disposable sterile packs.

Although applicant has described applicant's preferred embodiments of this invention, it will be understood that the broadest scope of this invention includes such modifications as diverse colors, shapes, sizes and materials. Such scope is limited only by the below claims as read in connection with the above specification. Further, many other advantages of applicant's invention will be apparent to those skilled in the art from the above descriptions and the below claims.

What is claimed is:

1. A holder system for comfortably and flexibly holding a port end of an indwelling catheter above a heart of a patient comprising:
   a) catheter cap means for releasably holding the port end of the indwelling catheter;
   b) hanging means for being suspended by a neck cord;
   c) wherein said hanging means comprises:
      i) said catheter cap means, and
      ii) connector means for connecting with the neck cord;
   d) wherein said hanging means further comprises a divider means, between said connector means and said catheter cap means, for assisting maintaining the sterility of the port end of the indwelling catheter.

2. The holder system according to claim 1 wherein said connector means comprises at least one aperture for holding the neck cord and said system further comprising:
   a) an adapter means for attaching with the neck cord and passing through said aperture.

3. The holder system according to claim 2 wherein said adapter means comprises a rigid bar portion suitable to pass through said aperture.

4. The holder system according to claim 1 further comprising suspending means for suspending said hanging means above the heart of the patient.

5. The holder system according to claim 4 wherein said suspending means comprises the neck cord.

6. The holder system according to claim 4 further comprising a second said hanging means, wherein each said hanging means is suspended by the same said suspending means.

7. The holder system according to claim 1 wherein said connector means comprises extension means, extending from a main body of said hanging means, for assisting connection with an eyeglass-holder neck cord.

8. A holder system to comfortably and flexibly hold a port end of an indwelling catheter above a heart of a patient comprising:
   a) a catheter cap structured and arranged to releasably hold the port end of the indwelling catheter;
   b) a hanger structured and arranged to be suspended by a neck cord;
   c) wherein said hanger comprises:
      i) said catheter cap; and,
      ii) at least one aperture structured and arranged to hold the neck cord;
   d) wherein said hanger further comprises a divider between said aperture and said catheter cap structured and arranged to assist maintaining sterility of the port end of the indwelling catheter.

9. The holder system according to claim 8 further comprising an adapter structured and arranged to pass through said aperture.

10. The holder system according to claim 9 wherein said adapter is structured and arranged to attach to the neck cord.

11. The holder system according to claim 8 wherein said divider comprises a dome.

12. The holder system according to claim 8 wherein said divider comprises a small hole structured and arranged to assist in preventing back air pressure on the catheter.

13. The holder system according to claim 8 wherein said hanger further comprises indicia.

14. The holder system according to claim 13 wherein said hanger further comprises a hook.

15. The holder system according to claim 14 wherein said indicia is removably attached to said hanger by hanging said indicia from said hook.

16. The holder system according to claim 13 wherein:
   a) said aperture comprises a sliding connection with the neck cord;
   b) said hanger comprises an anti-kinker to assist in preventing kinking in the indwelling catheter; and
   c) said hanger comprises essentially a disposable plastic material.

17. The holder system according to claim 16 further comprising a suspender structured and arranged to suspend said hanger above the heart of the patient.

18. The holder system according to claim 17 wherein said suspender comprises an eye-glass holder adapter constructed and arranged to fit through said at least one aperture.

19. The holder system according to claim 8 wherein said aperture comprises a sliding connection with the neck cord.

20. The holder system according to claim 8 wherein said hanger comprises a anti-kinker to assist in preventing kinking in the indwelling catheter.

21. The holder system according to claim 8 further comprising a suspender structured and arranged to suspend said hanger above the heart of the patient.

22. The holder system according to claim 21 wherein said suspender comprises the neck cord.

23. The holder system according to claim 21 further comprising at least one second said hanger, wherein each said hanger is suspended by the same said suspender.

24. The holder system according to claim 21 wherein said suspender further comprises an eye-glass holder adapter constructed and arranged to fit through said at least one aperture.

25. The holder system according to claim 24 wherein said eye-glass holder adapter comprises a rigid bar portion.

26. The holder system according to claim 8 wherein said aperture comprises an internally convex curve structured and arranged to assist said aperture to move slidingly along the neck cord.

27. The holder system according to claim 8 wherein said aperture comprises a tunnel shape.

28. The holder system according to claim 8 wherein said hanger comprises at least two apertures.

29. The holder system according to claim 8 wherein said aperture comprises a ring.

30. The holder system according to claim 8 wherein said hanger comprises essentially a disposable plastic material.

31. The holder system according to claim 8 wherein said hanger comprises jewelry-grade metal.

32. A holder system to comfortably and flexibly hold a port end of an indwelling catheter above a heart of a patient comprising:
   a) a catheter cap structured and arranged to releasably hold the port end of the indwelling catheter;
   b) a hanger structured and arranged to be suspended by a neck cord;
   c) wherein said hanger comprises:
      i) said catheter cap; and,
      ii) at least one aperture structured and arranged to hold the neck cord;
   d) wherein said hanger comprises an anti-kinker to assist in preventing kinking in the indwelling catheter;
   e) wherein said anti-kinker comprises a swivel connection between said catheter cap and said aperture.

33. The holder system according to claim 19 wherein said anti-kinker is structured and arranged to limit movement of said hanger with respect to the neck cord.

* * * * *